(12) United States Patent
Prescott

(10) Patent No.: US 7,501,396 B2
(45) Date of Patent: Mar. 10, 2009

(54) METHODS FOR TREATING JOINT PAIN USING POLY-GAMMA-GLUTAMIC ACID

(76) Inventor: Albert G. Prescott, 16 Lake Shore Dr. North, Westford, MA (US) 01886

( * ) Notice: Subject to any disclaimer, the term of this patent is extended or adjusted under 35 U.S.C. 154(b) by 429 days.

(21) Appl. No.: 11/425,824

(22) Filed: Jun. 22, 2006

(65) Prior Publication Data

US 2006/0234192 A1    Oct. 19, 2006

Related U.S. Application Data

(63) Continuation-in-part of application No. 10/974,442, filed on Oct. 27, 2004, now Pat. No. 7,364,875.

(60) Provisional application No. 60/693,263, filed on Jun. 23, 2005, provisional application No. 60/590,727, filed on Jul. 23, 2004, provisional application No. 60/515,879, filed on Oct. 30, 2003.

(51) Int. Cl.
*A01K 38/00* (2006.01)
*C12P 7/62* (2006.01)
*C12P 13/14* (2006.01)

(52) U.S. Cl. .................. 514/12; 435/110; 435/135; 514/2

(58) Field of Classification Search .............. None
See application file for complete search history.

(56) References Cited

OTHER PUBLICATIONS

Sabatini, M., et al. Effect of inhibition of matrix metalloproteinases on cartilage loss in vitro and in guinea pig model of osteoarthritis. Arthritis Rheum. Jan. 2005; 52(1):1.

Pelletier, J.P., et al. Osteoarthritis, an inflammatory disease: potential implication for the selection of new therapeutic targets. Arthritis Rheum. Jun. 2001; 44(6):1237-47.

*Primary Examiner*—Herbert J. Lilling
(74) *Attorney, Agent, or Firm*—Brian M. Dingman; Mirick, O'Connell, DeMallie & Lougee, LLP

(57) ABSTRACT

Methods for treating joint pain such as temporomandibular joint disorders, osteoarthritis of the knee, hip and other types of inflammatory joint diseases. The methods involve the use of poly-gamma-glutamic acid.

5 Claims, 1 Drawing Sheet

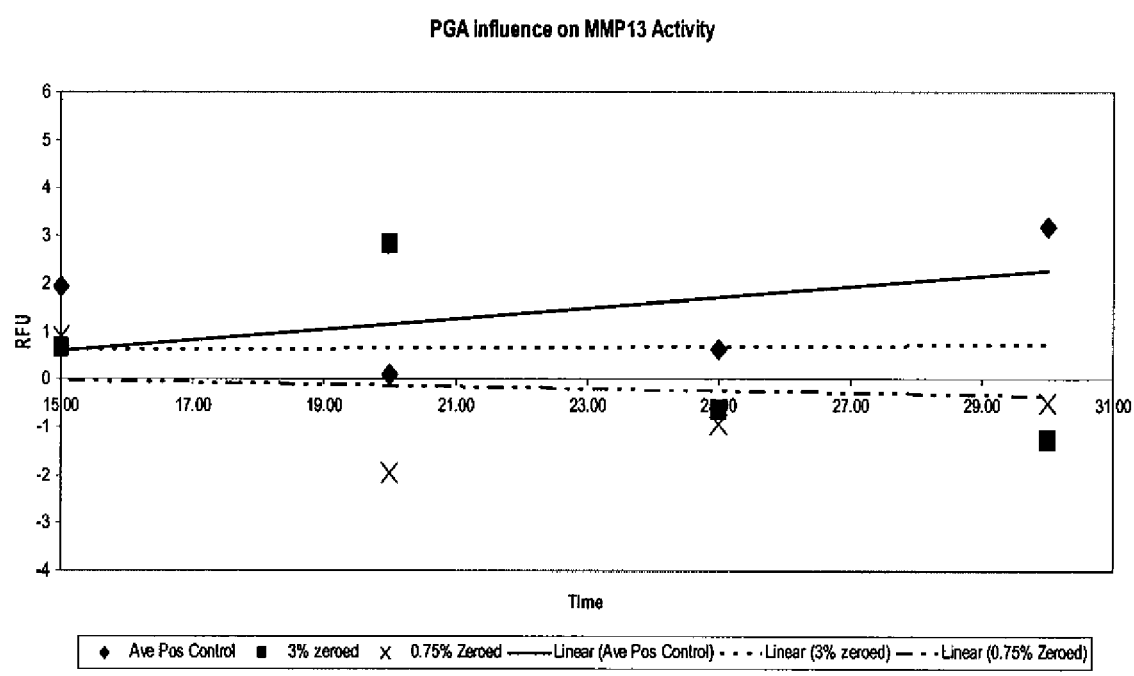

METHODS FOR TREATING JOINT PAIN USING POLY-GAMMA-GLUTAMIC ACID

CROSS-REFERENCE TO RELATED APPLICATIONS

This application claims priority of provisional application Ser. No. 60/693,263 filed on Jun. 23, 2005. This application is a continuation in part of, and thus also claims priority of, non-provisional application Ser. No. 10/974,442 filed on Oct. 27, 2004, now U.S. Pat. No. 7,364,875 which itself claims priority of provisional application 60/515,879 filed on Oct. 30, 2003 and 60/590,727 filed on Jul. 23, 2004.

FIELD OF THE INVENTION

This invention relates to methods for treating joint pain associated with inflammatory, degenerative and other joint diseases.

BACKGROUND OF THE INVENTION

Over 20 million people in the United States suffer from degenerative joint diseases. This results in over 2 million arthroscopic surgeries and about 250,000 knee and hip replacements each year. The result is a healthcare burden of over $1 billion dollars every year.

Degenerative joints are treated in the following manner:
Oral non-steroidal anti-inflammatory drugs (NSAIDs).
Visco-supplementation via interarticular hyaluronic acid injections.
Interarticular steroid injection.
Joint replacement.

This invention is related to visco-supplementation via interarticular injections. Currently all approved therapies of this type are comprised of hyaluronic acid or its sodium salt, commonly referred to as sodium hyaluronate, any one of which is herein referred to as HA. The explanations for the efficacy of HA vary. Some experts believe that HA provides benefits by lubricating the articular joint surfaces. Others believe it provides cushioning. Still others believe it is incorporated directly into the extra-cellular matrix of the synovial space, while still others believe it may provide a target, other than the joint tissues, for the inflammatory agents responsible for joint degeneration.

The flaw in these theories is that study after study has shown that the average residence time of HA injected into the synovial space is only 24 to 48 hours. There is no data to suggest that HA is incorporated into the extra-cellular matrix, and if HA vacates the space in only 24 to 48 hours, none of the other theories previously mentioned can explain the clinical data that HA provides 6 to 12 months of pain reduction. In order for HA to provide this level of benefit, some other mechanism must be at work.

It is theorized herein that the true mechanism behind the efficacy of HA is the poly-anionic nature of the molecule. Inflammatory cytokines, matrix-metallo-proteinases, and other biological molecules that are found in degenerative joints are proteins. Some proteins have a net negative charge, some have a net positive charge and some have a net neutral charge. Regardless of the net charge, all proteins have some portion that is positively charged. HA, on the other hand, is a polysaccharide that is fully negatively charged. Because of this, it is likely that the mechanism of efficacy is the extraction of inflammatory agents from the synovial tissues, electrostatic binding of these agents along the long chain of the HA molecule along its negatively charged carboxylic acid groups, and the subsequent removal of these agents when the HA vacates the synovial space.

If this theory is correct, it stands to reason that a biological polymer with a higher polyanionic charge density (i.e., more negative charges per equal mass of polymer) will be more efficacious at treating degenerative joint diseases than HA.

In order to test the efficacy of PGGA, inflammatory agents in OA were first identified. Various researchers have noted these agents [Sabatini M, Lesur C, Thomas M, Chomel A, Anract P, de Nanteuil G, Pastoureau P., "Effect of inhibition of matrix metalloproteinases on cartilage loss in vitro and in a guinea pig model of osteoarthritis", *Arthritis Rheum.* 2005 January; 52(1):171-80]. Of particular interest are the MMPs, and in particular, MMP-1, MMP-8, and MMP-13 which all have collagenase activity. This is because type 2 collagen in the main connective protein in the extra-cellular matrix of the cartilage in the knee and hip. All of these MMPs degrade this collagen, and hence, degrade the matrix and the cartilage.

Of the three MMPs, MMP-13 is the most potent and is selectively expressed in pathological conditions such as arthritis [Pelletier JP, Martel-Pelletier J, Abramson S B., "Osteoarthritis, an inflammatory disease: potential implication for the selection of new therapeutic targets", *Arthritis Rheum.* 2001 June; 44(6):1237-47]. Therefore, it makes sense that if a molecule, such as PGGA, inhibits the activity of MMP-13 it would likely protect the extra-cellular matrix and protect the cartilage. Such a molecule would make for a new and effective treatment for OA.

SUMMARY OF THE INVENTION

It is thus likely that poly-gamma-glutamic acid (PGGA), which has triple the charge density of HA, will be very efficacious at treating degenerative joint diseases such as OA of the knee, OA of the hip, and TMJ disorders.

The invention comprises methods for treating degenerative joint diseases via interarticular injections of poly-gamma-glutamic acid. The molecular weight of the PGGA is preferably greater than about 250,000 Daltons, though PGGA that is greater than 1 million Daltons is even more preferred. The reason is that the higher molecular weight forms have a longer half-life in the joint, thus more opportunity for efficacy. For example, the half life of HA with a molecular weight of around 1 million Daltons in the knee is about 17-20 hours.

BRIEF DESCRIPTION OF THE DRAWING

The accompanying drawing is a graph of the results of the experiment discussed below detailing PGGA influence over MMP-13 activity.

DETAILED DESCRIPTION OF THE PREFERRED EMBODIMENTS

Experiment

In order to test the MMP-13 theory discussed above, the following experiment was performed. An Enzolyte™ 490 MMP-13 Assay Kit (catalog number 71135) by AnaSpec Corporation was purchased. This kit measures MMP-13 activity by use of a fluorescent substrate. As the MMP-13 breaks down the substrate, a fluorescent molecule is released; the molecule may be measured via a fluorescent spectrometer at excitation/emission wavelengths of 340 nm/490 nm. As the MMP-13 continues to break this substrate down over time, the rate of reaction may be followed by graphing the Relative Fluorescent Units (RFU) versus time.

This test was performed in accordance with the Enzolyte™ 490 manual. The reaction was monitored with a SpectraMAX Gemini XS made by Molecular Devices. Reaction number 1 (see the accompanying figure) was a positive control containing just the substrate and active MMP-13. The other two reactions were performed, with all concentrations of MMP-13 and substrate the same, except that in one case 3% PGGA was used and in the other 0.75% PGGA was used. These concentrations were chosen because various commercial concentrations of HA solutions range from 0.8% (Synvisc®), to 1% (Hyalgan®) to 1.5% (Orthovisc®).

Results are reproduced in the drawing. The diamonds and the solid black line are the positive control. This represents the fluorescence increasing with time as the MMP-13 breaks down the substrate. The squares and the X's along with the two dashed lines represent little or no change in fluorescence. This means that PGGA prevented the MMP-13 from breaking down the substrate, leading to the conclusion that PGGA would be an effective treatment for OA.

The following is a description of the preferred embodiments of the invention. Non-inflammatory PGGA is produced via the methods described in the following examples. PGGA is then formulated aseptically, preferably at a concentration ranging from 10 mg/ml to 30 mg/ml, and most preferably at 15 mg/ml. The subsequent gel is then filled into a syringe for injection into the diseased joint.

The following are examples of production of the PGGA.

Example 1

PGGA Using Preferred Fermentation Method, and Purification to Medical Grade

Bacillus licheniformis ATCC 9945a was grown in Medium E. The fermentation was carried out at small scale, in shake flasks, at 37 C. Aeration was provided by diffusion. When the viscosity stopped rising (typically after about 3-5 days of fermentation), the fermentation broth was buffer exchanged via diafiltration using a filter with a molecular weight cut off (MWCO) of 30 kDa. The mixture of cells and PGGA was then buffered in citric acid, and micro-filtered using a filter with an opening of 0.22 microns, to remove the host cells.

The filtrate was neutralized, and buffer exchanged with pure water and concentrated via diafiltration using a filter with a MWCO of 30 kDa. Material from this purification may be sterile filtered.

To describe the process in more detail, when the viscosity stopped rising, the fermentation broth was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kda MWCO pore size. Five diafiltration volumes of solution were processed. At the end, the retentate was collected, sterilized by passing through a 0.22 micron filter, and precipitated in sterile ethanol and stored.

Material from this example has been used in rats in subsequent experiments with no inflammatory response. The molecular weight was determined to be 2 million Daltons using the following analytical MALLS method described in the Stock thesis that is incorporated by reference herein.

PGGA was dissolved at a concentration of 1 mg/ml in 0.1M citric acid, pH 2 to 3, with 0.05% sodium azide. The sample was degassed and 0.2 milliliters was injected at a flow rate of 0.5 mls/min. The SEC can utilize a TossoHaas TSK G5000PWXL, G6000PWXL, Waters Ultrahydrogel 1000 or 250. A Dawn DSP laser photometer from Wyatt technologies in conjunction with a Waters differential refractometer is used for detection.

This process is capable of making high molecular weight (when measured as described) poly-gamma-glutamic acid at purities up to and including pharmaceutical grade.

Example 2

PGGA from Another Commercial Source Purified

A sample reported to be poly-gamma-glutamic acid in excess of 1 million Daltons was received from an offshore commercial supplier. The viscosity of a sample of known concentration seemed to be lower than would be the case if the PGGA was indeed of the reported molecular weight. Analysis was impossible due to the large amount of contaminants, as evidenced by the off-white color noted when the sample was hydrated, and the fact that the hydrated sample had an odor similar to fermentation broth.

This material was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kda MWCO pore size. Five diafiltration volumes of solution were processed. The resulting material was clear and odorless, supporting the production of low molecular weight, high purity PGGA.

Example 3

PGGA

Bacillus licheniformis ATCC 9945a was grown in Medium E. The fermentation was carried out at small scale, in shake flasks, at 37 C. Aeration was provided by diffusion. When the viscosity stopped rising, the fermentation broth was buffer exchanged via diafiltration using a filter with a molecular weight cut off (MWCO) of 30 kDa. The mixture of cells and PGGA was then buffered in citric acid, and micro-filtered using a filter with an opening of 0.16 microns.

The filtrate was neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 4

PGGA

Bacillus licheniformis ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by passing the broth through a 0.22 micron TFF filter and collecting the filtrate. The filtrate was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 5

PGGA

Bacillus licheniformis ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by centrifugation at a speed over 10,000×g. The supernatant was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

What is claimed is:

1. A method of treating a degenerative joint disease, comprising:
   providing pharmaceutical grade poly-gamma-glutamic acid (PGGA);
   aseptically formulating the PGGA at a concentration of at least about 10 mg/ml;
   loading the aseptically formulated PGGA into a syringe; and
   placing the formulated PGGA into a diseased joint by interarticular injection.

2. The method of claim 1, wherein the PGGA has a molecular weight of at least about 250,000 Daltons.

3. The method of claim 2 wherein the PGGA has a molecular weight of at least about 1 million Daltons.

4. A method of treating a degenerative joint disease, comprising:
   providing pharmaceutical grade poly-gamma-glutamic acid (PGGA) having a molecular weight of at least about 250,000 Daltons;
   aseptically formulating the PGGA at a concentration of from about 10 mg/ml to about 30 mg/ml;
   loading the aseptically formulated PGGA into a syringe; and
   placing the PGGA into a diseased joint by interarticular injection.

5. The method of claim 4 wherein the PGGA has a molecular weight of at least about 1 million Daltons.

* * * * *